United States Patent [19]
Caggiano et al.

[11] Patent Number: 5,650,444
[45] Date of Patent: Jul. 22, 1997

[54] SUBSTITUTED BIPHENYL DERIVATIVES

[75] Inventors: Thomas J. Caggiano, Morrisville, Pa.; Joseph Prol, Jr., Champlain, N.Y.

[73] Assignee: American Home Products Corporation, Madison, N.J.

[21] Appl. No.: 452,593

[22] Filed: May 25, 1995

Related U.S. Application Data

[62] Division of Ser. No. 198,031, Feb. 17, 1994, abandoned.

[51] Int. Cl.$^6$ ............................................. A61K 31/15
[52] U.S. Cl. .................. 514/640; 514/682; 514/639; 514/638; 568/328; 568/442; 564/254; 564/253; 564/257; 564/251
[58] Field of Search .................. 514/639, 638, 514/640, 682; 568/328, 442; 564/254, 253, 251, 257

[56] References Cited

U.S. PATENT DOCUMENTS

| | | | |
|---|---|---|---|
| 2,716,663 | 8/1955 | Beman | 260/559 |
| 2,759,964 | 8/1956 | Beman | 260/473 |
| 2,921,939 | 1/1960 | Ramsdon | 260/295 |
| 3,043,746 | 7/1962 | Cavallini et al. | 167/65 |
| 3,120,551 | 2/1964 | Goldschmidt | 260/455 |
| 3,457,300 | 7/1969 | Dorn et al. | 260/515 |
| 3,624,142 | 11/1971 | Shen | 260/515 A |
| 3,671,580 | 6/1972 | Shen et al. | 260/520 |
| 3,681,445 | 8/1972 | Blank | 562/469 |
| 3,947,375 | 3/1976 | Gray et al. | 558/423 |
| 3,959,364 | 5/1976 | Armitage et al. | 260/515 A |
| 4,916,145 | 4/1990 | Tilley et al. | 514/357 |
| 5,087,743 | 2/1992 | Janssen et al. | 558/423 |
| 5,128,479 | 7/1992 | Janssen et al. | 558/423 |
| 5,177,067 | 1/1993 | Guerry et al. | 514/183 |

FOREIGN PATENT DOCUMENTS

| | | | |
|---|---|---|---|
| 0087340 | 8/1978 | Japan | 558/423 |

OTHER PUBLICATIONS

Kuroyanagi et al., "Further Characterization of the Constituents of a Thai Medicinal Plant, Zingiber Cassumunar Roxb.", Chem. Pharm. Bull., 28(10), pp. 2948–2959 (1980).
CA113(9):78171c (1990) Tilley et al.
CA111 (15): 133959b (1989) Tilley et al.
CA108 (5): 36953a (1988) Urban et al.
CA95 (9): 80661r (1981) Novasimbor et al.
CA93 (7):62827d (1980) Sparling et al.
CA75 (19): 115948f (1971) Kushnirenko et al.
CA67 (21):99464x (1967) Masso et al.
Derwent—Abstract of EP 422,597-A (1989) BASF.
Derwent—Abstract of ZA8505768 (1985), Merck.
Derwent—Abstract of J57032238 (1982) Hisamitsu.

*Primary Examiner*—James H. Reamer
*Attorney, Agent, or Firm*—Steven R. Eck

[57] ABSTRACT

A compound of the following structure:

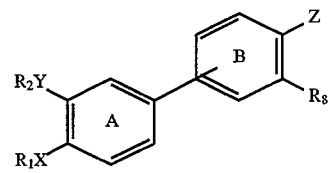

wherein, when $R_8$=H:
$R_1$=alkyl, cycloalkyl, arylalkyl, aryl;
$R_2$=cycloalkyl, aryl, $C_3$–$C_{10}$ alkyl;
X,Y=O, S(O)$_n$, NH;
Z=CHO, $CO_2R_3$, $CONHR_4R_5$, CN, $COR_6$, H, halo, HCN, $NHCONR_4R_5$, $CONR_4OR_5$, $CONR_4NR_5R_6$, 1-tetrazole, S(O)$_n$OH, S(O)$_n$NR$_3$R$_4$, C=NOH, C(=N(OH)NH$_2$, OCONR$_7$R$_6$, P(O)(OR$_4$)$_2$, C(=N(YR$_3$))R$_4$, NH$_2$, SH, OH, OS(O)$_2$R$_3$, C(=NYC(=O)R$_3$)R$_4$, C(O)CO$_2$R$_3$, C(O)CONR$_3$R$_4$, CH(OH)CO$_2$R$_3$, CHFCO$_2$R$_3$, CF$_2$CO$_2$R$_3$, CH(OH)CONR$_3$R$_4$, CF$_2$CONR$_3$R$_4$, C=NNH$_2$, C(=NOC(=O)R$_3$)R$_4$, C(=NNHC(=O)R$_3$)R$_4$, C(=NOH)R$_3$, C(=NNR$_3$)R$_4$, NHC(=O)R$_6$ or C(O)CONH$_2$;
$R_3$, $R_4$, $R_5$, $R_6$, $R_7$=hydrogen, alkyl, aryl, aryalkyl, cycloalkyl, or fluoroalkyl;
or a compound of Structure I, as just defined, wherein:
X,Y=CH$_2$, O, S(O)$_n$, or NH;
Z and $R_8$=CO$_2$R$_3$, CONR$_3$, or $R_8$ and Z are concatenated such that $R_8$Z=C(O)NHNHC(O), (CH$_2$)$_m$C(=W), V(CH$_2$)$_m$C(=W), or V$_n$CH=CH(CH$_2$)$_n$C(=W);
where
V=O, S(O)$_n$, NH;
W=O, NOH, NHNH$_2$, NOC(O)CH$_3$, or NNHC(O)CH$_3$;
n=0–2; and
m=2–4
or pharmaceutically acceptable salts thereof, useful in the treatment of asthma, and allergic and inflammatory diseases, as well as methods of treatment and pharmaceutical compositions utilizing the same.

18 Claims, No Drawings

SUBSTITUTED BIPHENYL DERIVATIVES

RELATED APPLICATIONS

This is a divisional application of application Ser. No. 08/198,031, filed Feb. 17, 1994, now abandoned.

BACKGROUND OF THE INVENTION

This invention relates to new methods of treating inflammatory diseases. More particularly, the present invention relates to new substituted biphenyl derivatives which are useful in the treatment of asthma, as well as other types of allergic and inflammatory diseases.

Asthmatic attacks are characterized by the narrowing of both large and small airways brought upon by bronchial smooth muscle spasms, edema and inflammation of the bronchial mucose, and production of tenacious mucus. The exact mechanisms involved in asthmatic bronchoconstriction are not completely understood, but an imbalance between beta adrenergic and cholinergic control of the airways has been indicated. Such imbalances appear to be controlled by the cyclic 3',5'-adenosine monophosphate (cyclic AMP or cAMP)-cyclic 3',5'-guanosine monophosphate (cyclic GMP or cGMP) systems with various tissues, such as smooth muscle, mast cells and mucus secreting cells.

Several classes of drugs have been shown useful in the treatment of bronchial asthma. They include the beta adrenergic agents which cause bronchial smooth muscle relaxation and modulate inhibition of mediator release. Among these agents are epinephrine, isoproterenol, ephedrine and beta$_2$-adrenergic agents such as metaproterenol, terbutaline, isoetharine, albuterol, bitolterol and fenoterol (5-[1-Hydroxy-2-[[2-(4-hydroxyphenyl)-1-methylethyl]amino]ethyl-1,3-benzenediol).

Corticosteroids, such as prednisone, have been useful in treating asthma as they inhibit attraction of polymorphonuclear leukocytes to the sites of allergic reactions, stimulate synthesis of beta$_2$ receptors and block leukotriene synthesis. Theophylline, a methyxanthine, has also been used for its ability to relax bronchial smooth muscle and modulate mediator release. Anticholinergic agents, such as atropine and its derivative ipratopium bromide, have been used to block cholinergic pathways that cause airway obstruction.

Used for maintenance therapy alone, cromolyn sodium (disodium cromoglycate) appears to inhibit mediator release and reduce airway hyperactivity.

In recent work, asthma has been recognized as being mediated by an inflammatory response in the respiratory tract [DeMonchy, J., Am. Rev. Resp. Dis. 131:373–376 (1985)]. Recent findings suggest that human T-lymphocytes play a major role in regulating the airway inflammation associated with allergic asthma [Frew, A. J., J. Allergy Clin. Immunol. 85: 533–539 (1990)] and chronic obstructive pulmonary disease [O'Connor, G. T., Am. Rev. Resp. Dis. 140:225–252 (1989)].

In addition to the infiltration of other inflammatory cells into the pulmonary system, human asthmatics and atopics who are dual responders (i.e., show both early and late phase reactions) show a small but significant infiltration of T-lymphocytes following antigen challenge [Frew, A. J. and Kay, A. B., J. Immunol. 141:4158–4164 (1988)]. More importantly, these recruited T-lymphocytes are almost entirely of the CD4$^+$ (T-helper) type, and there appears to be a direct correlation between the influx of CD4$^+$ cells, the influx of eosinophils, and the IgE-related allergic response in these individuals [Frew, A. J. and Kay, A. B., J. Immunol. 141:4158–4164 (1988)]. In severe asthmatics, these CD4$^+$ cells appear to be activated [Corrigan, C. J. and Kay, A. B., Am. Rev. Resp. Dis. 141:970–977 (1990)] by virtue of the increase in IL-2 receptor positive cells. Thus, these cells are capable of producing cytokines (such as IL-3, IL-5, and granulocyte macrophage colony stimulating factor) which can directly affect the differentiation, maturation and activation state of the eosinophils and other inflammatory cells.

Rapamycin, a macrocyclic triene antibiotic produced by *Streptomyces hygroscopicus* [U.S. Pat. No. 3,929,992] has been shown to prevent the formation of humoral (IgE-like) antibodies in response to an albumin allergic challenge [Martel, R., Can. J. Physiol. Pharm. 55:48 (1977)], inhibit murine T-cell activation [Strauch, M., FASEB 3:3411 (1989)].

BRIEF DESCRIPTION OF THE PRESENT INVENTION

This invention relates to compounds demonstrated to inhibit a specific phosphodiesterase (PDE), often called PDE IV, that selectively metabolizes cyclic adenosine 3':5'-monophosphate (cAMP) and that is insensitive to the modulatory effects of guanosine cyclic 3':5' monophosphate (cGMP) and calcium. This PDE is found in both respiratory smooth muscle and inflammatory cells, and has been demonstrated to be a principle regulator of cAMP in these tissues [see Torphy and Cieslinski, *Molecular Pharmacology*, 37, 206 (1990)), and Dent et al., *British Journal of Pharmacology*, 90, 163P (1990)]. Consequently, the compounds named in this invention are both bronchodilatory and antiinflamatory, and are effective in animal models of allergic and nonallergic asthma. However, because the compounds named in this invention preferentially inhibit the PDE IV isozyme, they are expected to be more selective and safer anti-asthmatics than nonselective PDE inhibitors currently used for the treatment of asthma, such as theophylline.

These compounds are inhibitors of the enzyme 3', 5' cyclic AMP phosphodiester-ase. By virtue of this activity, the compounds act as bronchodilators as well as prevent the influx of leukocytes into the lung and pulmonary cavities of antigen sensitized and subsequently challenged laboratory animals. Thus these compounds are useful for the acute and chronic treatment of bronchial asthma and its associated pathology.

This invention describes the composition and utility of novel biphenyl compounds, and their pharmaceutically acceptable salts, of the general structure I:

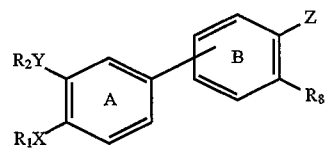

wherein, when $R_8$=H:

$R_1$=alkyl, cycloalkyl, arylalkyl, aryl;

$R_2$=cycloalkyl, aryl, $C_3$-$C_{10}$ alkyl;

X,Y=O, S(O)$_n$, NH;

Z=CH$_2$OH, NHSO$_2$R$_3$, CHO, CO$_2$R$_3$, CONHR$_4$R$_5$, CN, COR$_6$, H, halo, NHCN, NHCONR$_4$R$_5$, CONR$_4$OR$_5$, CONR$_4$NR$_5$R$_6$, 1-tetrazole, S(O)$_n$OH, S(O)$_n$NR$_3$R$_4$, C=NOH, C(=N(OH)NH$_2$, OCONR$_7$R$_6$, P(O)(OR$_4$)$_2$, C(=N(YR$_3$))R$_4$, NH$_2$, SH, OH, OS(O)$_2$R$_3$, C(=NYC(=O)R$_3$)R$_4$, C(O)CO$_2$R$_3$, C(O)CONR$_3$R$_4$, CH(OH)CO$_2$R$_3$, CHFCO$_2$R$_3$, CF$_2$CO$_2$R$_3$, CH(OH)CONR$_3$R$_4$, $CF_2CONR_3R_4$, $C=NNH_2$, $C(=NOC(=O)R_3)R_4$, $C(=NNHC(=O)R_3)R_4$, $C(=NOH)R_3$, $C(=NNR_3)R_4$, $NHC(=O)R_6$ or $C(O)CONH_2$;

$R_3$, $R_4$, $R_5$, $R_6$, $R_7$=hydrogen, alkyl, aryl, aryalkyl, cycloalkyl, or fluoroalkyl;

or a compound of Structure I, as just defined, wherein:

$R_1$=alkyl, cycloalkyl, arylalkyl, or aryl;

$R_2$=cycloalkyl, aryl, or alkyl;

$X,Y=CH_2$, O, $S(O)_n$, or NH;

$R_3$, $R_4$, $R_5$, $R_6$, $R_7$=hydrogen, alkyl, aryl, arylalkyl, cycloalkyl, or fluoroalkyl;

$R_8=CO_2R_3$, $CONR_2R_3$, or $R_8$ and Z are concatenated such that $R_8Z=C(O)NHNHC(O)$, $(CH_2)_mC(=W)$, $V(CH_2)_mC(=W)$, or $V_nCH=CH(CH_2)_nC(=W)$;

where

V=O, $S(O)_n$, NH;

W=O, NOH, $NHNH_2$, $NOC(O)CH_3$, or $NNHC(O)CH_3$;

halo=Cl, Br, or I;

fluoroalkyl=$CF_3$ $CHF_2$, $CH_2F$, $CH_2CF_3$, $C_2F_5$;

cycloalkyl=$C_3$–$C_6$ cycloalkyl;

arylalkyl=$C_{1-C4}$ aryl;

aryl=phenyl, furanyl, thienyl, or pyridyl;

n=0–2; and m=2–4.

Among these compounds is a more narrow group including those having the structure presented above wherein, when $R_8$=H:

$R_1$=alkyl, cycloalkyl, arylalkyl, aryl;

$R_2$=cycloalkyl, aryl, $C_3$–$C_{10}$ alkyl;

$X,Y$=O, $S(O)_n$, NH;

Z=$CH_2OH$, $NHSO_2R_3$, CHO, CN, $COR_6$, H, halo, NHCN, $NHCONR_4R_5$, $S(O)_nOH$, $S(O)_nNR_3R_4$, C=NOH, $C(=N(OH)NH_2$, $OCONR_7R_6$, $P(O)(OR_4)_2$, $C(=N(YR_3))R_4$, $NH_2$, SH, OH, $OS(O)_2R_3$, $C(=NYC(=O)R_3)R_4$, $C=NNH_2$, $C(=NOC(=O)R_3)R_4$, $C(=NNHC(=O)R_3)R_4$, $C(=NOH)R_3$, $C(=NNR_3)R_4$, $NHC(=O)R_6$ or $C(O)CONH_2$;

$R_3$, $R_4$, $R_5$, $R_6$, $R_7$=hydrogen, alkyl, aryl, aryalkyl, cycloalkyl, or fluoroalkyl;

or a compound of Structure I, as just defined, wherein:

$R_1$=alkyl, cycloalkyl, arylalkyl, or aryl;

$R_2$=cycloalkyl, aryl, or alkyl;

$X,Y=CH_2$, O, $S(O)_n$, or NH;

$R_3$, $R_4$, $R_5$, $R_6$, $R_7$=hydrogen, alkyl, aryl, arylalkyl, cycloalkyl, or fluoroalkyl;

$R_8=CO_2R_3$, $CONR_2R_3$, or $R_8$ and Z are concatenated such that $R_8Z=C(O)NHNHC(O)$, $(CH_2)_mC(=W)$, $V(CH_2)_mC(=W)$, or $V_nCH=CH(CH_2)_nC(=W)$;

where

V=O, $S(O)_n$, NH;

W=O, NOH, $NHNH_2$, $NOC(O)CH_3$, or $NNHC(O)CH_3$;

halo=Cl, Br, or I;

fluoroalkyl=$CF_3$ $CHF_2$, $CH_2F$, $CH_2CF_3$, $C_2F_5$;

cycloalkyl=$C_3$–$C_6$ cycloalkyl;

arylalkyl=$C_{1-C4}$ aryl;

aryl=phenyl, furanyl, thienyl, or pyridyl;

n=0–2; and m=2–4.

Preferred examples of the present invention may be described by the general structure II:

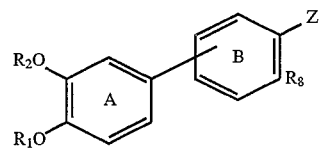

wherein:

$R_1$=$C_1$–$C_3$ alkyl;

$R_2$=$C_3$–$C_6$ alkyl, $C_3$–$C_7$ cycloalkyl, or phenyl;

Z=CHO, $CO_2R_3$, $CONHR_4R_5$, CN, $COR_6$, H, halo, $NHCONR_4R_5$, $CONR_4OR_5$, $CONR_4NR_5R_6$, $OCONR_7R_6$, $C(+N(YR_3))R_4$, $NH_2$, C=NOH, $C=NNH_2$, $C(=NOC(=O)R_3)R_4$, $C(=NNHC(=O)R_3)R_4$, $C(O)CO_2R_3$, $C(=NOH)R_3$, $C(=NNR_3)R_4$, $NHC(=O)R_6$, or $C(O)CONH_2$; and $R_3$, $R_4$, $R_5$, $R_6$, $R_7$=hydrogen, $C_1$–$C_4$ alkyl, aryl, arylalkyl, fluoroalkyl; and $R_8$=H or $CO_2R_3$;

as well as pharmaceutically acceptable salts thereof.

In these preferred compounds, it is further preferred that ring A is attached to ring B in the meta or para position.

In addition, preferred examples of this invention may be described by the formula II, above, wherein ring B is described by structures III or IV, seen below, and is attached to ring A at the 5, 6 or 7 position of ring B.

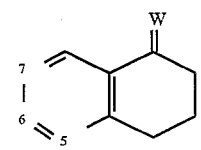

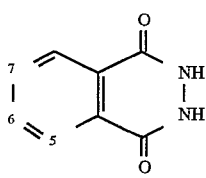

wherein W=O, NOH, $NNH_2$, $NOC(O)CH_3$, $NNHC(O)CH_3$.

For the compounds listed, unless otherwise stipulated, alkyl =$C_1$–$C_6$; halo=Cl, Br, or I; fluoroalkyl=$CF_3$, $CHF_2$, $CH_2F$, $CH_2CF_3$ or $C_2F_5$; cycloalkyl=$C_3$–$C_6$ cycloalkyl; arylalkyl=$C_1$–$C_4$ substituted aryl; and aryl=phenyl, furanyl, thienyl or pyridyl.

Among the more preferred compounds of this invention are those having the general structure:

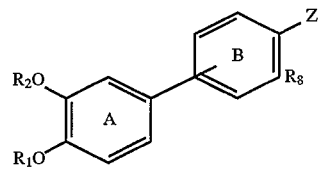

wherein:

$R_1$=$C_1$–$C_3$ alkyl;

$R_2$=$C_3$–$C_7$ cycloalkyl or $C_3$–$C_6$ alkyl;

Z=$CO_2R_3$, $CONHR_4R_5$, $CONR_4NR_5R_6$, H, halo, CHO, $COR_6$, CN, $NH_2$, $NHCONR_4R_5$, $CONR_4OR_5$, $C(=N(YR_3))R_4$, $OCONR_7R_6$, $C(=NOH)R_3$, $C(=NNR_3)R_4$, $C(=NOC(=O)R_3)R_4$, $C(=NNHC(=O)R_3)R_4$, or $NHC(=O)R_6$;

$R_3$, $R_4$, $R_5$, $R_6$, $R_7$=H, $C_1$–$C_4$ alkyl, aryl, or trifluoromethyl; and $R_8$=H or $CO_2R_3$;
or pharmaceutically acceptable salts thereof.

It is also understood that these preferred compounds of the present invention may also include those in which ring B is described by structures III or IV, above, and is attached to ring A at the 5, 6 or 7 position.

The most preferred compounds of the present invention may be described by the formula:

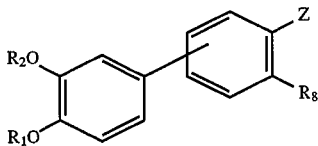

wherein:

$R_1$=$CH_3$;

$R_2$=$C_4$ alkyl, $C_5$ cycloalkyl;

Z=meta or para CHO, $CO_2R_3$, $CONHR_4R_5$, CN, $COR_6$, H, chloro, bromo, $NHCONR_4R_5$, $CONR_4OR_5$, $CONR_4NR_5R_6$, $OCONR_6R_7$, $NH_2$, C(=NOH)$R_3$, C(=NN$R_3$)$R_4$, C(=NOC(=O)$R_3$)$R_4$, C(=NNHC(=O)$R_3$)$R_4$;

$R_3$, $R_4$, $R_5$, $R_6$, and $R_7$=hydrogen, methyl, phenyl, or trifluoromethyl; and $R_8$=hydrogen;

or pharmaceutically acceptable salts thereof.

These most preferred compounds also include those in which $R_9$ and Z are $CO_2R_3$ or $CONR_4R_5$. In addition, the most preferred compounds of the present invention may be described by the formulas V and VI, below, or pharmaceutically acceptable salts of the compounds of formulas V and VI:

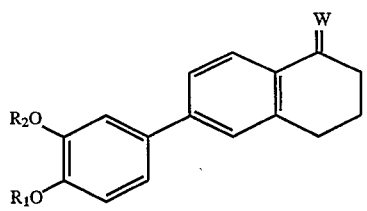 V

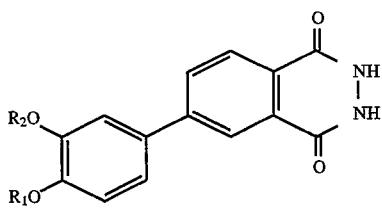 VI wherein $R_1$, $R_2$, and W are as described above.

These compounds show activity against PDE IV isolated from dog tracheal muscle with $IC_{50}$s in the range of $10^{-6}$ to $10^{-9}$M. These compounds also show activity in the functional PDE inhibitory test with $IC_{50}$s in the range of $10^{-6}$ to $10^{-8}$M. More information concerning these tests and their indications of the present compounds PDE IV inhibitory ability is set forth in Example 35, below.

Also provided by the present invention is a method for treating allergic and inflammatory diseases, as well as asthma, both allergic and non-allergic. Such a method comprises administering to a mammal in need of such treatment an effective amount of one or more of the compounds listed herein and/or one or more of their pharmaceutically acceptable salts. Such a method 5s intended to include all treatments, administrations, or regimens related to such maladies including, but are not limited to, those which are prophylactic, therapeutic, progression inhibiting, remedial, maintenance, or other treatments regarding asthma and allergic and inflammatory disease states or conditions.

The effective dosages of the compounds presented herein will vary with the particular compound chosen and the form of administration. Furthermore, it will vary with the particular host under treatment. Generally, the compounds of this invention are administered at a concentration level that affords protective effects without any deleterious side effects. For example, the effective amount of compound can usually range from about 10 to about 250 mg/kg body weight per day administered once daily or divided into two to four administrations per week. The optimum dosage for the individual subject being treated will be determined by the person responsible for treatment, generally with smaller doses being administered initially and thereafter increases in dosage are made to determine the most suitable dosage.

Further embraced by the present invention are pharmaceutical compositions. Among these are compositions comprising a mixture of one or more of the compounds disclosed herein, and/or one or more pharmaceutically acceptable salts thereof, and a pharmaceutically acceptable carrier, which can be used according to the same methods of administration as the compounds, themselves. It is also contemplated that the compounds of the present invention may be used in a combined therapeutic regimen along with one or more additional medicinal agents.

The compounds of the present invention may form salts with suitable therapeutically acceptable inorganic and organic bases. These derived salts possess the same activity as their parent acid and are included within the scope of this invention. Suitable inorganic bases to form these salts include, for example, the hydroxides, carbonates or bicarbonates of the therapeutically acceptable alkali metals or alkaline earth metals such as lithium, sodium, potassium, magnesium, calcium and the like. Suitable organic bases include primary and secondary amines such as methylamine, benzathine (N,N$^1$-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) procaine, etc. Furthermore, there may be mentioned the quaternary salts, for example, the tetraalkyl (e.g. tetramethyl), alkyl-alkanol (e.g. methyl-triethanol) and cyclic (e.g. N,N-dimethylmorpholine) ammonium salts. In principle, however, there can be used all the ammonium salts which are physiologically compatible.

Transformations to the corresponding salts are readily carried out by reacting the acid form of the compounds with an appropriate base, usually one equivalent, in a cosolvent. The salt is isolated by concentration to dryness or by addition of a non-solvent. For example, in the case of inorganic salts, it is preferred to dissolve the acid or the compound in water containing a hydroxide, carbonate or bicarbonate corresponding to the inorganic salt desired. Evaporation of the solution or addition of a water-miscible solvent of more moderate polarity, for example, a lower alkanol such as butanol, or a lower alkanone such as ethyl methyl ketone, gives the solid inorganic salt. In the case of an amine salt, it is preferred to use a cosolvent of moderate or low polarity such as ethanol, ethylacetate and benzene. Evaporation of the solvent or addition of a miscible diluent of lower polarity such as benzene or n-hexane gives the solid salt. Quaternary ammonium salts may be prepared by mixing the acid of the compound with a quaternary ammonium hydroxide in a water solution followed by evaporation of the water.

The compounds of the present invention may be clinically administered to mammals, including man, by either the oral or parenteral route. Oral administration may be either alone or in combination with a solid or liquid pharmaceutically acceptable carrier or diluent such as starch, milk, sugar, certain types of clay, water, vegetable or mineral oils, and so forth to form tablets, capsules, powders, syrups, solutions, suspensions, and the like. For parenteral administration, the active compounds may be used in combination with aqueous or organic media to form injectable solutions or suspensions. For example, solutions in sesame or peanut oil, aqueous solutions of water and soluble pharmaceutically acceptable salts of the compounds. The injectable solutions prepared in this manner may be administered intravenously, intraperitoneally, subcutaneously or intramuscularly. The compounds of this invention may also be administered in the form of suppositories.

Compounds of this invention may be prepared in the manner shown in the schemes below:

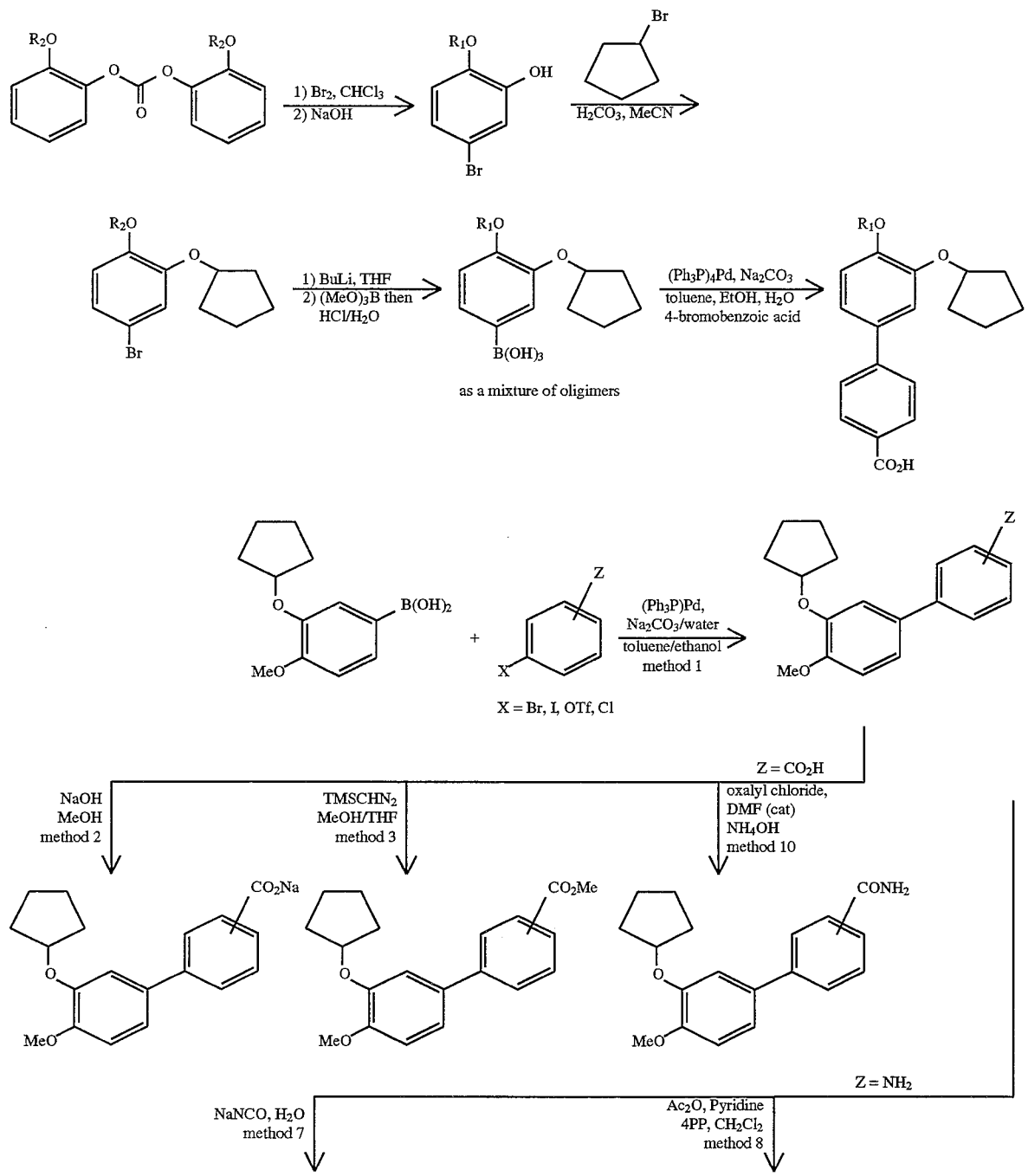

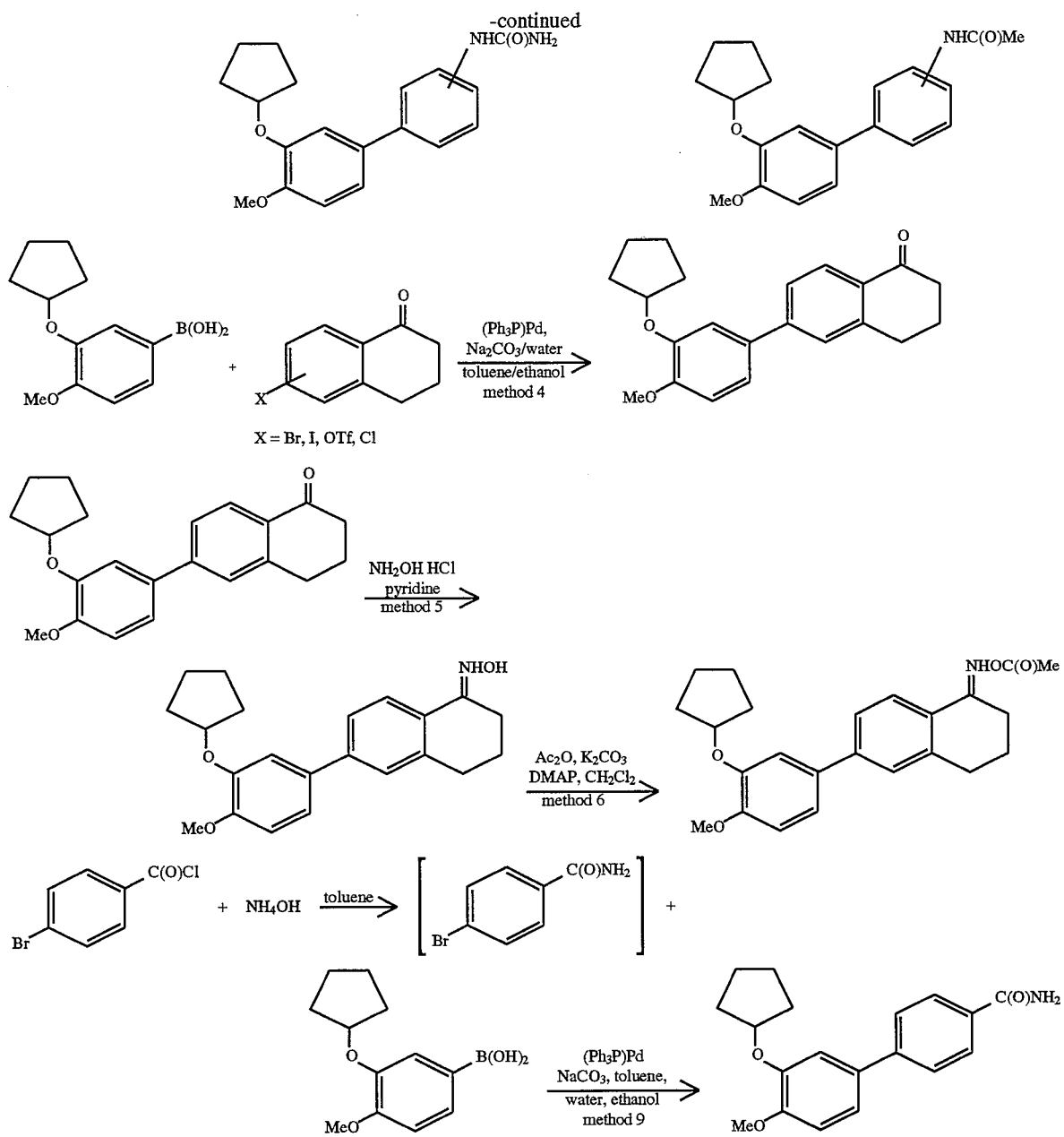

Additional information regarding the synthesis and efficacy of the present invention's compounds is provided by the non-limiting examples below:

EXAMPLE 1

3-Cyclopentyloxy-4-methoxybromobenzene

Cyclopentyl bromide (37 mL, 0.345 mol) was added to a slurry of the phenol (50 g, 0.246 mol) and potassium carbonate (17 g, 0.123 mol) in acetonitrile (500 mL) at reflux temperature. After two hours, cyclopentyl bromide (13.2 mL, 0.123 mol) and potassium carbonate (8.5 g, 0.062 mol) were added to complete the reaction (1 hour). Reaction progress was monitored by TLC (50% ethyl ether in hexane). The suspension was filtered. The filtered material was washed with ethyl acetate (2×100 mL). The filtrates were combined, concentrated and distilled under vacuum (0.1 mm, 140° C.°145° C.) to yield 65.62 g (0.242 mol, 98%) of product.

3-Cyclopentyloxy-4-methoxyphenylboronic acid.

3-Cyclopentyloxy-4-methoxyphenylbromide (25 g, 0.0923 mol) was dissolved in dry THF (400 mL) in a flame dried flask under nitrogen. The solution was stirred and cooled (−78° C.). n-Butyllithium (2.5M in THF, 42.44 mL, 0.106 mol) was added over 15 minutes with a raise in temperature to no higher than −50° C. The reaction was allowed to stir 2 hours at −78° C. Trimethylborate (28.76 mL, 0.277 mol) was added over 5 minutes. The reaction was allowed to warm toward ambient room temperature over two hours. HCl (1N, 300 mL, 0.3 mol) was added and the reaction was stirred 18 hours. Reaction pro- gress was monitored by TLC (50% ethyl acetate in hexane). The product was extracted with ethyl ether (3×150 mL). The combined organic layers were washed with water (150 mL); brine (150 mL); and were dried (magnesium sulfate). The concentrated product is used crude. Yield was essentially "quantitative".

IR (KBr) 3420 cm$^{-1}$; NMR (DMSO/D$_2$O) δ 7.32 (d, 1H, J=7.89) 7.28 (s, 1H) 6.9 (d, 1H, J=7.89) 4.72 (m, 1H) 3.70 (s,3H) 1.84–1.51 (m, 8H); MS (+FAB) m/z: 237 (M+H).

3'-Cyclopentyloxy-4'-methoxy-biphenyl-4-carboxylic acid.

3-Cyclopentyloxy-4-methoxyphenylboronic acid (1 g, 4.25 mmol), 4-bromobenzoic acid (897 mg, 4.46 mmol), sodium carbonate (1.5 g), toluene (30 mL), water (12 mL), and ethanol (6 mL) were added to a flask at room temperature and stirred. The reaction was flushed with nitrogen. The catalyst, tetrakistriphenylphospine palladium (0) (100 mg) was added. The reaction was heated at reflux temperature sixteen hours. At that time the catalyst turned to a black suspension. The reaction was monitored by TLC (50% ethyl acetate in hexane) and was complete when the catalyst was dead. The reaction was diluted with ethyl acetate (50 mL) and NaOH (0.5N, 50 mL). The organic phase was separated and extracted with NaOH (0.5N, 2×50 mL). The combined aqueous was acidified with HCl (2.5N) until red to litmus. The precipitate was extracted with ethyl acetate (3×50 mL). The combined organic layers were washed with brine and dried (magnesium sulfate). The organic layers were boiled with activated charcoal and filtered through a bed of silica atop a bed of celite. The resulting clear organic was concentrated to dryness. Recrystallization (ethyl acetate/hexane) yielded 1.0 g of product (3.21 mmol, 75.4%): mp 231.5° C.–232.5° C.

IR (KBr) 2960, 1670 cm$^{-1}$; NMR (DMSO) δ 12.89 (1H, s), 7.96 (2H, d, J=8.5 Hz), 7.74 (2H, d, J=8.5 Hz), 7.26 (1H, d, J=8.2 Hz), 7.24 (1H, s), 7.04 (1H, d, J=8.2 Hz), 4.93 (1H, m), 3.78 (3H, s), 2.0–1.5 (8H, m); MS m/z: 312 (M$^+$), 244 (100);

Elemental analysis for: C$_{19}$H$_{20}$O$_4$ Calc'd: C, 73.06; H, 6.45 Found: C, 72.73; H, 6.45

EXAMPLE 2

3'-Cyclopentyloxy-4'-methoxy-biphenyl-4-carboxylic acid amide

Following the procedure of Example 1, 4-bromobenzoic acid amide yielded 21% of the title compound a white solid.

IR (KBr) 3400, 3180, 1670, 1640 cm$^{-1}$; NMR (CDCl$_3$) δ 7.88 (2H, d, J=8.4 Hz), 7.62 (2H, d, J=8.4 Hz), 7.17 (1H, d, J=8.30 Hz), 7.13 (1H, d, J=2.1 Hz), 6.95 (1H, d, J=8.3 Hz), 4.33 (1H, m), 3.89 (3H, s), 2.0–1.6 (8H, m); MS m/z: 311 (M$^+$);

Elemental analysis for: C$_{19}$H$_{21}$NO$_3$.H$_2$O Calc'd: C, 69.3; H, 6.38; N, 4.25 Found: C, 70.79; H, 6.40; N 3.12

EXAMPLE 3

3'-Cyclopentyloxy-4'-methoxy-biphenyl-4-carboxylic acid hydrazide

Following the procedure of Example 1, 4-bromobenzoic acid hydrazide yielded 81% of the title compound as colorless crystals: mp 167°–168.5° C.

IR (KBr) 3300, 1600 cm$^{-1}$; NMR (DMSO) δ 9.78 (1H, s), 7.86 (2H, d, J=8.4 Hz), 7.69 (2H, d, J=8.4 Hz), 7.24 (1H, d, J=8.1 Hz), 7.22 (1H, d, J=8.1 Hz), 7.02 (1H, d, J=8.1 Hz), 4.93 (1H, m), 4.49 (2H, s), 3.77 (3H, s), 2.0–1.5 (8H, m); MS m/z 277 (M+H), 294 (100);

Elemental analysis for: C$_{19}$H$_{22}$N$_2$O$_3$ Calc'd: C, 69.92: H, 6.79; N, 8.58 Found: C, 69.62;H, 6.82; N, 8.55

EXAMPLE 4

3'-Cyclopentyloxy-4'-methoxy-biphenyl-3-carboxylic acid hydrazide

Following the procedure of Example 1, 3-bromobenzoic acid hydrazide yielded 25% of the title compound as colorless crystals: mp 167°–168.5° C.

IR (KBr) 3310, 3390, 1645 cm$^{-1}$; NMR (DMSO) δ 9.87 (1H, s), 8.01 (1H, s), 7.75 (2H, m), 7.49 (1H, t, J=8.6 Hz), 7.25 (2H, m) 7.04 (1H, d, J=8.9 Hz), 4.94 (1H, m), 4.51 (1H, s), 3.78 (3H, s), 2.0–1.5 (8 H, m); MS m/z: 326 (M$^+$), 227 (100).

Elemental analysis for: C$_{19}$H$_{22}$N$_2$O$_3$C, 69.92 Calc'd: C, 69.92:H, 6.79; N, 8.58 Found: C, 69.16; H, 6.75; N, 8.21

EXAMPLE 5

3'-Cyclopentyloxy-4'-methoxy-biphenyl-3-carboxylic acid

Following the procedure of Example 1, 3-bromobenzoic acid yielded 37% of the title compound as colorless crystals from ether: mp 153°–154° C.

IR (KBr) 3420, 3100–2500 (br) cm$^{-1}$; NMR DMSO δ 13.03 (1H, s), 8.11 (1H, m) 7.87 (2H, m), 7.55 (2H, t, J=8 Hz), 7.21 (1 H, m), 7.19 (1H, s), 7.05 (1H, d, J=7.9 Hz), 4.93 (1H, m), 3.78 (3 H, s), 2.0–1.5 (8H, m); MS m/z: 313 (M+H), 245 (100).

Elemental analysis for: C$_{19}$H$_{20}$O$_4$ Calc'd: C, 73.06: H, 6.45 Found: C, 72.23: H, 6.42

EXAMPLE 6

4-Chloro-3'-Cyclopentyloxy-4'-methoxy-biphenyl

Following the procedure of Example 1, 4-chlorophenylboronic acid and 3-cyclopentyloxy-4-methoxybromobenzene yielded 92% of the title compound as white needles: mp 94°–95° C.

IR (KBr) 2950 cm$^{-1}$; NMR (CDCl$_3$) δ 7.45 (2H, d, J=8.5 Hz), 7.36 (2H, d, J=8.5 Hz), 7.07 (1H, dd, J=8.1 Hz), 7.05 (1H, s), 6.91 (1H, d, J=8.1 Hz), 4.83 (1H, m), 3.87 (3H, s), 1.98–1.55 (8 H, m); MS m/z: 303 (M$^+$), 235 (100).

Elemental analysis for: C$_{18}$H$_{19}$ClO$_2$ Calc'd: C, 71.40; H, 6.32 Found: C, 71.24; H, 6.41

EXAMPLE 7

3-Cyclopentyloxy-4-methoxy-biphenyl

Following the procedure of Example 1, phenylboronic acid and 3-cyclopentyloxy-4-methoxybromobenzene yielded 46% of the title compound as white needles: mp 62°–64° C.

IR (KBr) 2960 cm$^{-1}$; NMR (CDCl$_3$) δ 7.53 (2H, d, J=7.06 Hz), 7.40 (2H, t, J=7.5 Hz), 7.29 (1H, t, J=7.5 Hz), 7.10 (2 H, m), 6.92 (1H, d, J=7.5 Hz), 4.85 (1H, m), 3.87 (3H,s), 1.98–1.52 (8 H,m); MS m/z: 268 (M$^+$), 200 (100).

Elemental analysis for: C$_{18}$H$_{20}$O$_2$ Calc'd: C, 80.58; H, 7.51 Found: C, 79.86; H, 7.49

EXAMPLE 8

3'-Cyclopentyloxy-4'-methoxy-biphenyl-3-carbaldehyde

Following the procedure of Example 1, 3-bromobenzaldehyde yielded 40% of the title compound as an amorphous solid.

IR (KBr) 1720, 1690 cm$^{-1}$; NMR (CDCl$_3$) δ 10.08 (1H, s), 8.04 (1H, t, J=1.5 Hz), 7.82 (1H, d, J=7.6 Hz), 7.81 (1H, d, J=7.4 Hz), 7.58 (1H, t, J=7.7 Hz), 7.18 (1H, dd, J=2.2, 8.2

Hz), 7.14 (1H, d, J=2.2 Hz), 6.96 (1H, d, J=8.2 Hz), 4.88 (1H, m), 3.90 (3H, s), 2.02–1.56 (8H, m); MS m/z: 296 (M$^+$), 228 (100).

Elemental analysis for: $C_{19}H_{20}O_3$ Calc'd: C, 77.00; H, 6.80 Found: C, 76.85; H, 6.91

EXAMPLE 9

3'-Cyclopentyloxy-4'-methoxy-biphenyl-4-carbaldehyde

Following the procedure of Example 1, 4-bromobenzaldehyde yielded 28% of the title compound as a crystalline solid: mp 86.5°–87.5° C.

IR (KBr) 1705 cm$^{-1}$; NMR δ 10.04 (1H, s), 7.93 (2H, d, J=8.5 Hz), 7.70 (2H, d, J=8.5 Hz), 7.20 (1H, dd, J=2.1,8.4 Hz), 7.17 (1H, d, J=2.1 Hz), 6.96 (1H, d, J=8.4 Hz), 4.87 (1H, m), 3.90 (3H, s), 2.06–1.6 (8 H,m); MS m/z: 296 (M$^+$), 228 (100).

Elemental analysis for: $C_{19}H_{20}O_3$ Calc'd: C, 77.00; H, 6.80 Found: C, 76.84; H, 6.76

EXAMPLE 10

3'-Cyclopentyloxy-4'-methoxy-biphenyl-2-carbaldehyde

Following the procedure of Example 1, 2-bromobenzaldehyde yielded 59% of the title compound as a yellow oil.

IR (film) 1695 cm$^{-1}$; NMR DMSO δ 9.91 (1H, s), 7.87 (1H, d, J=7.6 Hz), 7.71 (1H, dt, J=7.7, 1.5 Hz), 7.53 (2H, m), 7.07 (1H, d, J=8.3 Hz), 6.98 (1H, d, J=2.1 Hz), 6.91 (1H, dd, J=8.3, 2.1 Hz), 4.85 (1H, m) 3.80 (3H, s) 1.93–1.5 (8H m); MS m/z: 296 (M$^+$), 228 (100, M–C$_5$H$_9$).

Elemental analysis for: $C_{19}H_{22}O_3$ Calc'd: C, 77.00; H, 6.80 Found: C, 75.89; H, 6.86

EXAMPLE 11

1-(3'-Cyclopentyloxy-4'-methoxy-biphenyl-3-yl)-ethanone

Following the procedure of Example 1, 3-bromoacetophenone yielded 53% of the title compound as a viscous yellow oil.

IR (film) 1680 cm$^{-1}$; NMR (DMSO) δ 8.10 (1H, t, J=1.6), 7.89 (2H, m), 7.57 (1H, t, J=7.7), 7.23 (2H, m), 7.05 (1H, d, J=8.1 Hz), 4.93 (1H, m), 3.78 (3H, s), 2.64 (3H, s), 1.95–2.5 (8H, m); MS m/z: 310 (M$^+$), 242 (100).

Elemental analysis for: $C_{20}H_{22O3}$ Calc'd: C, 77.35; H, 7.14 Found: C, 74.99; H, 7.19

EXAMPLE 12

1-(3'-Cyclopentyloxy-4'-methoxy-biphenyl-4-yl)-ethanone

Following the procedure of Example 1, 4-bromoacetophenone yielded 42% of the title compound as a crystalline solid: mp 117°–118° C.

IR (KBr) 1670 cm$^{-1}$; NMR (DMSO) δ 7.99 (2H, d, J=8.5 Hz), 7.77 (2H, d, J=8.5 Hz), 7.28 (1H, dd, J=8.3, 2 Hz), 7.25 (1H, d, J=2.4 Hz), 4.94 (1H, m), 3.79 (3H, s) 2.59 (3H, s), 2.0–1.5 (8 H, m); MS m/z: 310 (M$^+$), 242 (100).

Elemental analysis for: $C_{22}H_{22}O_3$ Calc'd: C, 77.39; H, 7.14 Found: C, 74.99; H, 7.19

EXAMPLE 13

(3'-Cyclopentyloxy-4'-methoxy-biphenyl-4-yl)-phenylmethanone

Following the procedure of Example 1, 4-bromobenzophenone yielded 37% of the title compound as a viscous oil in 38% yield.

IR (film) 1650 cm$^{-1}$; NMR (DMSO) δ 7.8 (6H, m), 7.68 (1H, t, J=1.2 Hz), 7.58 (2H, t, J=7 Hz), 7.3 (2H, m), 7.08 (1H, d, J=8.3 Hz), 4.95 (1H, m), 3.80 (3H, s); MS m/z: 372 (M$^+$), 304 (100).

Elemental analysis for: $C_{25}H_{24}O_3$ Calc'd: C, 80.62; H, 6.50 Found: C, 79.53; H, 6.79

EXAMPLE 14

3'-Cyclopentyloxy-4'-methoxy-biphenyl-3-carbonitrile

Following the procedure of Example 1, 3-bromobenzonitrile yielded 25% of the title compound as an amorphous solid.

IR (KBr) 2220 cm$^{-1}$; NMR (DMSO) δ 8.1 (1H, s), 7.98 (1H, d, J=8.1 Hz), 7.75 (1H, d, J=7.7 Hz), 7.61 (1H, t, J=7.7 Hz), 7.28 (2H, m), 7.04 (1H, d, J=8.5 Hz), 4.97 (1H, m), 3.8 (3H, s); MS m/z: 293 (M$^+$), 225 (100).

Elemental analysis for: $C_{18}H_{19}NO_2$ Calc'd: C, 76.84; H, 6.81; N, 4.98 Found: C, 77.62; H 6.51; N, 4.54

EXAMPLE 15

3'-Cyclopentyloxy-4'-methoxy-biphenyl-4-carbonitrile

Following the procedure of Example 1, 4-bromobenzonitrile yielded 56% of the title compound as a crystalline solid. mp 97–98.5.

IR (KBr) 2200 cm$^{-1}$; NMR (CDCl$_3$) δ 7.69 (2H, d, J=8.7 Hz), 7.62 (2H, d, J=8.7), 7.13 (1H, dd, J=8.3 2.2 Hz), 7.08 (1H, d, J=2.2 Hz), 6.95 (1H, d, J=8.3 Hz), 4.85 (1H, m), 3.89 (1H, s), 2.05–1.58 (8H, m); MS m/z: 294 (M$^+$, 100).

Elemental analysis for: $C_{19}H_{19}NO_2$ Calc'd: C, 77.79; H, 6.53; N, 4.77 Found: C, 78.08; H, 6.59; N, 4.82

EXAMPLE 16

3'-Cyclopentyloxy-4'-methoxybiphenyl-4-ylamine

Following the procedure of Example 1, 4-bromoaniline yielded 55% of the title compound as a crystalline solid. mp 94°–95° C.

IR (KBr) 3460, 3380 cm$^{-1}$; NMR (DMSO) δ 7.43 (2H, d, J=8.6 Hz), 7.05 4H, m), 6.90 (2H, d, J=8.6 Hz), 4.84 (1H, m), 3.87 (3H, m), 2.0–1.5 (8H, m); MS m/z: 283 (M$^+$), 215 (100).

Elemental analysis for: $C_{18}H_{21}NO_2$ Calc'd: C, 76.30: H, 7.47; N, 4.94 Found: C, 76.03; H, 7.45; N, 4.64

EXAMPLE 17

3'-Cyclopentyloxy-4'-methoxy-biphenyl-4-carboxylic acid sodium salt

3'-Cyclopentyloxy-4'-methoxybiphenyl-4-carboxylic acid (0.5 g, 1.6 mmol) was suspended in H$_2$O (5 mL). A solution of sodium hydroxide (1.6 mL, 1M, 1.6 mmol) was added and the reaction was heated to ca 90° C. for 30 seconds. Product was concentrated to dryness, dissolved in hot methanol (25 mL) precipitated from solution with ethyl ether and filtered. The filter cake was washed with ether and hexane then pumped under high vacuum to constant weight. This provided 0.354 g (1.06 mmol, 66%) of product.

IR (KBr) 3400 cm$^{-1}$; NMR (DMSO) δ 7.89 (2H, d, J=8.5 Hz), 7.49 (2H, d, J=8.5 Hz), 7.18 (1H, d, J=8.92 Hz), 7.18 (2H, m), 7.01 (1H, d, J=8.92 Hz), 4.91 (1H, m), 3.77 (3H, s), 2.0–1.5 (8H, m); MS [–FAB] m/z: 311 (M–Na)$^-$.

Elemental analysis for: $C_{19}H_{19}O_4Na$ Calc'd: C, 68.26; H, 5.73 Found: C, 63.32; H, 5.61

EXAMPLE 15

3'-Cyclopentyloxy-4'-methoxy-biphenyl-3-carboxylic acid methyl ester

3'-Cyclopentyloxy-4'-methoxy-biphenyl-3-carboxylic acid (0.2 g, 0.64 mmol) in THF/MeOH (1:1, 10 mL) was cooled to 0° C. To this was added a solution of trimethylsilyldiazomethane in hexane until TLC (1:1 ethyl acetate/hexane) showed no more starting material. The solvents were removed and the product was purified using radial chromatography (1000 μm silica, 30% ethyl acetate in hexane as eluant). This yielded 150 mg (79%) of the title product as a crystalline solid. mp 85°–87° C.

IR (KBr) 3420, 1710 cm$^{-1}$; NMR δ 8.22 (1H, t, J=1.6 Hz), 7.97 (1H, dt, J =: 7.6, 1.5 Hz), 7.39, (1H, dt, J=7.6, 1.5 Hz), 7.48 (1H, t, J=7.9 Hz), 7.16 (1H, dd, J=8.2, 2.1 Hz), 7.13 (1H, d, J=2.1 Hz), 4.87 (1H, m), 3.95 (3H, s), 3.89 (3H, s), 2.20–1.6 (8H,m); MS m/z: 326 (M$^+$), 258 (100).

Elemental analysis for: $C_{20}H_{22}O_4$ Calc'd: C, 73.60; H, 6.79 Found: C, 73.53; H, 6.80

EXAMPLE 19

3'-Cyclopentyloxy-4'-methoxy-biphenyl-4-carboxylic acid methyl ester

Following the method described in Example 18, 3'-cyclopentyloxy-4'-methoxy-biphenyl-4-carboxylic acid yielded the title compound in 71% yield as a crystalline solid: mp 128°–131° C.

IR (KBr) 1720 cm$^{-1}$; NMR (CDCl$_3$) δ 8.04 (2H, d, J=8.6 Hz), 7.61 (2H, d,J=8.6 Hz), 7.17 (1H, dd J=8.32, 3 Hz), 7.15 (1H, d, J=2.3 Hz), 6.95 (1H, d, J=8.3 Hz), 4.87 (1H, m), 3.93 (3H, s), 3.90 (3H, s), 2.05–1.55 (8H, m); MS m/z: 326 (M$^+$), 258 (100).

Elemental analysis for: $C_{20}H_{22}O_4$ Calc'd: C, 73.60; H, 6.79 Found: C, 73.46; H. 6.83

EXAMPLE 20

6-(3-Cyclopentyloxy-4-methoxy-phenyl)-3,4-dihydro-2H-naphthalen-1-one

3-Cyclopentyloxy-4-methoxyphenylboronic acid (0.76 g, 3.23 mmol), 6-trifluoromethanesulfonate-3,4,-dihydro-2H-naphthalen-1-one (0.95 g, 3.23 mmol), sodium carbonate (1.0 g), toluene (30 mL), water (12 mL), and ethanol (6 mL) were added to a flask at room temperature and stirred. The reaction was flushed with nitrogen. The catalyst, tetrakistriphenylphospine palladium(0) (100 mg) was added. The reaction was heated at reflux temperature sixteen hours. At that time the catalyst turned to a black suspension. The reaction was monitored by TLC (50% ethyl acetate in hexane), however, completion of the reaction was obvious when the catalyst turned black. The reaction was diluted with ethyl acetate (50 mL). The organic phase was separated and extracted with water (50 mL). The organic phase was washed with brine and dried (magnesium sulfate). The organic phase was boiled with activated charcoal and filtered through a bed of silica atop a bed of celite. The resulting clear organic phase was dried (magnesium sulfate), filtered, concentrated to dryness. Recrystallization, from ethyl acetate/hexane, yielded 0.41 g (1.22 mmol, 38%) of product: mp 91° C.–92.5° C.

IR (KBr) 1670 cm$^{-1}$; NMR (DMSO) δ 7.90 (1H, d, J=8.9 Hz), 7.60 (2H, m), 7.25 (2H, m), 7.05 (1H, d, J=8.9 Hz), 4.94 (1H, m), 3.79 (3H, s), 3.0 (2H, c, J=6 Hz), 2.60 (2H, t, J=6 Hz), 2.05 (2H, m), 2.0–1.5 (8H, m); MS m/z: 337 (M+H), 269 (100, M–C$_5$H$_9$).

Elemental analysis for: $C_{22}H_{24}O_3$ Calc'd: C, 78.54; H, 7.19 Found: C, 78.38; H, 7.22

EXAMPLE 21

(E)-6-(3-Cyclopentyloxy-4-methoxy-phenyl)-3,4-dihydro-2H-naphthalen-1-one oxime 6-(3-Cyclopentyloxy-4-methoxy-phenyl)-3,4-dihydro-2H-naphthalen-1-one (0.17 g, 0.51 mmol), hydroxylamine hydrochloride (0.175 g, 2.51 mmol), and pyridine (1.0 mL) were added to a flask at room temperature and stirred sixteen hours. The reaction was dissolved in dichloromethane and concentrated to dryness. Ethyl acetate (25 mL) was added and the resulting solution was washed with water (25 mL), brine (25 mL), dried (magnesium sulfate), filtered, concentrated to dryness and recrystallized from ethyl acetate/hexane. Yield of product (0.1 g, 0.285 mmol, mp 151°–152° C.); 56%.

IR (KBr) 3250 cm$^{-1}$; NMR (DMSO) δ11.06 (1H, s), 7.88 (1H, d, J=8.1 Hz), 7.44 (1H, d, J=7.9 Hz), 7.43 (1H, s) 7.19, (1H, d, J=7.9 Hz), 7.18 (1H, s), 7.01 (1H, d, J=8.1 Hz), 4.92 (1H, m), 3.77 (3H, s), 2.77 (2H, t, J=3.8 Hz), 2.66 (2H, t, J=6.3 Hz); MS m/z: 351 (M$^+$), 283 (100).

Elemental analysis for: $C_{22}H_{25}NO_3$ Calc'd: C, 75.18; H, 7.17; N, 3.98 Found: C, 74.84; H, 7.13; N, 3.96

EXAMPLE 22

3'-Cyclopentyloxy-4'-methoxy-biphenyl-4-carbaldehyde oxime

Following the procedure in Example 21, one 3'-cyclopentyloxy-4'-methoxy-biphenyl-4-carbaldehyde yielded the title compound in 26% as a crystalline solid: mp 153°–153° C.

IR (KBr) 3450, 3300 cm$^{-1}$; NMR (DMSO) δ 11.2 (1H, s), 8.15 (1H, s), 7.65 (4H, m), 7.21 (1H, d, J=8.7 Hz) 7.20 (1H, s), 7.02 (1H, d, J=8.7 Hz), 4.92 (1H, m), 3.77 (3H, s), 2.0–1.5 (8H, m); MS m/z: 311 (M$^+$), 225 (100).

Elemental analysis for: $C_{19}H_{21}NO$ Calc'd: C, 73.29; H, 6.80; N, 4.50 Found: C, 72.60; H, 6.66; N, 4.35

EXAMPLE 23

3'-Cyclopentyloxy-4'-methoxy-biphenyl-3-carbaldehyde oxime

Following the procedure in Example 21, 3'-cyclopentyloxy-4'-methoxy-biphenyl-3-carbaldehyde yielded the title compound in 45% as a crystalline solid mp 87°–91° C.

IR (KBr) 3420, 3300 cm$^{-1}$; NMR (DMSO) δ 8.20 (1H, s), 7.74 (1H, s), 7.57 (1H, dr, J=7.9, 2.6 Hz), 7.52 (1H, dr, J=7.9, 2.6 Hz), 7.44 (1H, d, J=8.6 Hz), 7.38 (1H, s), 7.14 (1H, d, J=2.2 Hz), 7.12 (1H, d, J=2.2 Hz), 6.94 (1H, d, J=8.6 Hz), 4.86 (1H, m), 3.89 (3H, s), 2.0–1.58 (8H, m); MS m/z: 311 (M$^+$), 243 (100).

Elemental analysis for: $C_{19}H_{21}NO_3$ Calc'd: C,73.29; H,6.80; N, 4.50 Found: C, 73.14; H, 6.78; N, 4.47

EXAMPLE 24

3'-Cyclopentyloxy-4'-methoxy-biphenyl-2-carbaldehyde oxime

Following the procedure in Example 21, 3'-cyclopentyloxy-4'-methoxy-biphenyl-2-carbaldehyde yielded the title compound in 45% as a low melting (<50° C.) white solid.

IR (KBr) 3440 cm$^{-1}$ NMR (DMSO) δ 11.2 (1H, s), 7.94 (1H, s), 7.83 (1H, d, J=8.7 Hz), 7.20 (3H, m), 7.04 (1H, d,

J=8.1 Hz), 6.81 (2H, m), 4.80 (1H, m), 3.79 (3H, s), 1.9–1.5 (8 H, m) MS m/z: 311 (M$^+$), 226 (100)

Anal. Calcd for $C_{19}H_{21}NO_3$: C, 73.29; H, 6.80; N, 4.50. Found: C, 72.40; H, 6.89; N, 4.52.

EXAMPLE 25

E-6-(3-Cyclopentyloxy-4-methoxy-phenyl)-3,4-dihydro-2H-naphthalen-1-one oxime acetate E-6-(3-Cyclopentyloxy-4-methoxy-phenyl) -3,4-dihydro-2H-naphthalen-1-one oxime (0.08 g, 0.228 mmol), acetic anhydride (2 mL), potassium carbonate and dichloromethane (25 mL) were added to a flask and heated to reflux for 0.5 hours. The reaction was cooled and was washed with water (25 mL), brine (25 mL), dried (magnesium sulfate), filtered, concentrated to dryness and recrystallized from ethyl acetate/hexane. This yielded 0.053 g (0.134 mmol, 59%) of product: mp 100°–102° C.

IR (KBr) 3400, 1750 cm$^{-1}$; NMR (DMSO) δ 7.99 (1H, d, J=1.4 Hz), 7.54 (1H, d, J=7.5 Hz), 7.53 (1H, s), 7.25 (1H, d, J=7.5 Hz), 7.22 (1H, s), 7.03 (1H d, J=8.3 Hz), 4.93 (1H, m) 3.78 (3H, s), 2.83 (2H, t, J=3.7 Hz); MS m/z: 393 (M$^+$), 283 (100).

Elemental analysis for: $C_{24}H_{28}NO_4$ Calc'd: C, 73.07; H, 7.15; N, 3.55 Found: C, 72.62; H, 7.01; N, 3.57

EXAMPLE 26

(3'-Cyclopentyloxy-4'-methoxy-biphenyl-4-yl)-urea

3'-Cyclopentyloxy-4'-methoxybiphenyl-4-ylamine (0.283 g, 1.0 mmol) was dissolved in acetic acid (4.8 mL). A solution of sodium isocyanate in water (9 mL) was added. The precipitate formed was dissolved in dichloromethane (25 mL) washed saturated sodium bicarbonate (25 mL) with water (25 mL), brine (25 mL), dried (magnesium sulfate), filtered, and concentrated. Precipitation from dichloromethane. yielded 0.155 g (0.475 mmol, 61.2%) of product as an amorphous solid.

IR (KBr) 3420, 1657 cm$^{-1}$; NMR (DMSO) δ 8.56 (1H, s), 7.45 (4H, dd, J=6.6, 5.1 Hz), 7.0 (2H, m), 6.96 (1H, d, J=8.9 Hz), 5.83 (2H, s), 4.88 (1H, m), 3.74 (3H, s); MS m/z: 327 (M+H), 257 (100).

Elemental analysis for: $C_{19}H_{22}N_2O_3$ Calc'd: C, 69.92; H, 6.79; N, 8.58 Found: C, 68.53; H, 7.09; N, 7.91

EXAMPLE 27

(3'-Cyclopentyloxy-4'-methoxy-biphenyl-3-yl)-urea

Following the procedure in Example 26, 3'-cyclopentyloxy-4'-methoxy-biphenyl-3-yl amine yielded the title compound in 79% yield as a crystalline solid ($CH_2Cl_2$). mp 174°–175° C.

IR (KBr) 3390, 1700 cm$^{-1}$; NMR (DMSO) δ 8.56 (1H, s), 7.59 (1H, t, J=1.9) 7.32 (1H, d, J=7.90 Hz), 7.24 (1H, t, J=7.8 Hz), 7.1 (2H, m), 7.01 (1H, d, J=9 Hz), 5.85 (1H, s), 4.86 (1H, m), 3.76 (3H, s); MS m/z: 326 (M$^+$), 241 (100).

Elemental analysis for: $C_{19}H_{22}N_2O_3.H_2O$ Calc'd: C, 66.33; H, 7.03; N, 8.14 Found: C, 66.17; H, 6.45; N, 8.06

EXAMPLE 28

N-(3'-Cyclopentyloxy-4'-methoxy-biphenyl-4-yl)-acetamide

3'-Cyclopentyloxy-4'-methoxybiphenyl-4-ylamine (0.220 g, 0.78 mmol), pyridine (0.189 mL, 2.33 mmol), and acetic anhydride were dissolved in dichloromethane (25 mL). 4-pyrrolidinopyridine (1 mg) was added and the reaction was stirred 2 hours. The reaction was washed with saturated sodium bicarbonate (25 mL), water (25 mL), brine (25 mL), dried (magnesium sulfate), filtered, and concentrated to dryness. Product was recrystallized from ethyl acetate/hexane. Yield of product (0.170 g, 0.523 mmol); 67% as an amorphous solid.

IR (KBr) 3300, 1620 cm$^{-1}$; NMR (DMSO) δ 7.54 (2H, d, J=8.3 Hz), 7.49 (2;t, d, J=8.3 Hz), 7.26 (1H, s), 7.10 (1H, d, J=8.9 Hz), 7.08 (1H, s), 6.92 (1H, d, J=8.9 Hz), 4.84 (1H, m), 3.88 (3H, s), 2.20 (3H, s); MS m/z: 325 (M$^+$), 257 (100).

Elemental analysis for: $C_{20}H_{23}NO_3$ Calc'd: C, 73.82; H, 7.12; N, 4.30 Found: C, 73.23; H; 7.07; N, 4.10

EXAMPLE 29

N-(3'-Cyclopentyloxy-4'-methoxy-biphenyl-3-yl)-acetamide

Following the procedure of Example 28, 3'-cyclopentyloxy-4'-methoxy-biphenyl-3-yl amine yielded the title compound in 82% as a crystalline solid: mp 112°–114° C.

IR (KBr) 3290, 1660 cm$^{-1}$; NMR (CDCl$_3$) δ 7.67 (1H, s), 7.46 (1H, d, J=7.4 Hz), 7.36 (1H, t, J=7.8 Hz), 7.25 (2H, m), 7.10 (2H, m), 6.92 (1H, d, J=8.8 Hz), 4.85 (1H, m), 3.88 (3H, s), 2.20 (3H, s); MS m/z: 325 (M$^+$), 257 (100).

Elemental analysis for: $C_{20}H_{23}NO_3$ Calc'd: C, 73.82; H, 7.12; N, 4.30 Found: C, 73.78; H; 7.13; N, 4.19

EXAMPLE 30

3'-Cyclopentyloxy-4'-methoxy-biphenyl-3-carboxylic acid amide

A solution of 3-bromobenzoyl chloride in toluene (30 mL) is treated with concentrated ammonium hydroxide (2 mL) at room temperature for ten minutes. This mixture is then treated with 3-cyclopentylox-4-methoxy-phenyl boronic acid (0.5 g, 2.12 mmol), sodium carbonate (1 g), ethanol (10 mL) and tetrakis-(triphenylphosphine) palladium (25 mg). The reaction was warmed at reflux overnight under a nitrogen blanket. This provided the title compound in 34% as a crystalline solid (ethyl acetate/hexane): mp 133°–135° C.

IR (KBr) 3300, 3150, 1660 cm$^{-1}$; NMR (DMSO) δ 8.07 (2H, m), 7.79 (1H, d, J=7.8 Hz), 7.75 (1H, d, J=7.8 Hz), 7.49 (1H, t, J=7.6 Hz), 7.41 (1H, br s), 7.24 (2H, m), 7.04 (1H, d, J=9.2 Hz), 4.94 (1H, m), 3.78 (3H, s), 2.0–1.5 (8H, m); MS m/z: 311 (M$^+$), 243 (100).

Elemental analysis for: $C_{19}H_{21}NO_3$ Calc'd: C, 73.29; H, 6.80; N, 4.50 Found: C, 72.64; H, 6.94; N, 4.34

EXAMPLE 31

3'-Cyclopentyloxy-4'-methoxy-biphenyl-4-carboxylic acid hydroxylamide

A solution of 3'-cyclopentyloxy-4'-methoxy-biphenyl-4-carboxylic acid (0.5 g, 1.602 mmol) in toluene (30 mL) was treated with a 2M solution of oxalyl chloride (0.840 mL, 1.68 mmol) in dichloromethane and 1 drop of dimethyl formamide was added. This mixture was heated to reflux for ten minutes, cooled and concentrated in vacuo to an oil. This oil is dissolved in dichloromethane and added dropwise to a mixture of hydroxylamine hydrochloride (0.139 g, 1.25 eq) and triethylamine (0.405 g, 2.5 eq) in dichloromethane (10 mL). After about thirty minutes the reaction the reaction appears to go no further, some of the starting acid remains (by tlc). The reaction is washed with water dried and concentrated. The material is purified via reversed phase HPLC, using a Dynamax-60A Phenyl column wand 70% acetonitrile/water as carrier. This provided the title compound in 9% yield as a crystalline solid ($CH_2Cl_2$). mp 181°–183° C.

IR (KBr) 3225, 1620 cm$^{-1}$; NMR (DMSO) δ11.24 (1H,s), 9.01 (1H,s), 7.80 (2H,d, J=8.5 Hz), 7.70 (2H, d, J=8.5 Hz), 7.24 (1H, d, J=8.3 Hz), 7.22 (1H, s), 7.04 (1H, d, J=8.3 Hz), 4.94 (1H, m), 3.78 (3H, s); MS m/z: 327 (M$^+$), 227 (100).

Elemental analysis for: $C_{19}H_{21}NO_4$ Calc'd: C, 69.71; H, 6.47; N, 4.28 Found: C, 69.54; H, 6.44; N, 3.81

EXAMPLE 32

3'-Cyclopentyloxy-4'-methoxy-biphenyl-3,4-dicarboxylic acid

Following the procedure of Example 1, 4-bromophthalic acid yielded 25% of the title compound a white powder, mp 143°–146° C.

IR (KBr) 3500–2500(br), 1720, 1680 cm$^{-1}$ NMR (DMSO) δ13 (1H, br s), 7.83 (1H, s), 7.80 (H, d, J=1.8 Hz), 7.76 (1H, d, J=8.1 Hz), 7.26 (1H, d, J=6.0 Hz), 7.25 (1H, s), 7.05 (1H, d, J=8.5 Hz), 4.96 (1H, m), 3.79 (3H, s), 1.9 (2H, m), 1.74 (4H, m), 1.58 (2H, m) MS (FAB) 357 (M+H)$^+$

Elemental analysis for: $C_{20}H_{20}O_6$ Calc'd: C, 67.41; H, 5.66 Found: C, 65.79; H, 6.00

EXAMPLE 33

3'-Cyclopentyloxy-4'-methoxy-biphenyl-3,4-dicarboxylic acid dimethyl ester

A solution of the diacid (120 mg, 0.33 mmol) prepared above is dissolved in ether (20 ml) and cooled to 0° C. To this was added an etherial solution of diazomethane until the yellow color persisted. The solution was stirred for 10 minutes and then glacial acetic acid was added to discharge the color. The solvent was removed in vacuo. The sample was chromatographed on silica gel with ethyl acetate in hexanes. This provided the product as an oil (118 mg, 93%).

IR (film) 1725 cm$^{-1}$ NMR (DMSO) δ7.91 (1H, d, J=4.8 Hz), 7.90 (1H, s), 7.82 (1H, d, J=4.5 Hz), 7.30 (1H, d, J=2.1 Hz), 7.28 (1H, s), 7.06 (1H, d, J=8.1 Hz), 4.96 (1H, m), 3.84, (3H, s), 3.83 (3H, s), 3.70 (3H, s), 1.89 (2H, m), 1.72 (4H, m), 1.57 (2H, m) MS (CI) 385 (M+H)$^+$ Elemental analysis for: $C_{22}H_{24}O_6$ Calc'd: C, 68.74; H, 6.29 Found: C, 68.18; H, 6.49

EXAMPLE 34

6-(3'-Cyclopentyloxy-4'-methoxyphenyl)-2,3-dihydrophthalizine-1,4-dione

The diacid prepared above (1.05 g, 2.94 mmol) was dissolved in acetic anhydride (10 ml) in a Carius tube. The tube was heated in a 140° C. oil bath for 30 minutes, cooled and the solvent removed in vacuo. The crude anhydride was dissolved in dry dichloromethane (10 ml) and hydrazine hydrate was added (0.2 ml). The mixture was refluxed overnight with a Dean Stark trap. The sample was then diluted with 1N NaOH and was extracted with ethyl acetate. The organic layer was discarded and the aqueous layer was acidifed with concentrated HCL. The resulting solid was filtered to give the product (1.02 g, 98%) as a dihydrate (mp>255° C.).

IR (KBr) 1665 cm$^{-1}$ NMR (DMSO δ8.23 (1H, s), 8.09 (2H, s), 7.30 (2H, m), 7.08 (1H, d, J=8.3 Hz), 4.95 (1H, m), 3.80 (3H, s), 1.90 (2H, m), 1.75 (4H, m), 1.60 (2H, m) MS (EI) 352 (M$^+$)

Elemental analysis for: $C_{20}H_{20}N_2O_4 \cdot 2H_2O$ Calc'd: C, 61.84; H, 6.23; N, 7.21 Found: C, 61.86; H, 5.22; N, 7.07

EXAMPLE 35

The following standard tests are employed to assess the abilities of compounds to inhibit PDE IV in vitro.

Test Procedure No. 1

A solution containing PDE IV is prepared from canine tracheal muscle as follows:

The dog is euthanized with an overdose of beuthanasia while under anesthesia induced by a 33 mg/kg IV bolus of Nembutal. The trachealis muscle is removed, cleaned of connective tissue, and minced thoroughly. Three to four grams of tissue is then homogenized in Tris-HCl buffer (pH 7.8) using a Polytron. The homogenate is then centrifuged at 25,000×g (4° C.) for 30 minutes. The supernatant is decanted and filtered through four layers of gauze, and applied to a 40 cm×2 cm DEAE-Sepharose column that is equilibrated with Tris-HCl buffer (pH 7.8). The column is then washed with an additional 240 mL of buffer to remove unbound proteins. PDE is eluted using 450 mL of Tris-HCl buffer containing a linear gradient of 0.0–1.0M Na-acetate (80 mL/hr), and 7.5 mL fractions are collected. Each fraction is assayed for cAMP- and cGMP-metabolizing PDE activity. Fractions eluting at approximately 0.6M Na-acetate, and containing cAMP but not cGMP metabolic activity are pooled and used as a PDE stock solution for assaying PDE IV inhibitory activity.

PDE IV activity is tested as described previously [see Thompson et al., *Advances in Cyclic Nucleotide Research*, 10, 69 (1979)] at 30° C. in a reaction mixture containing: 10 mM Tris-HCl (pH 7.8), 5 mM $MgCl_2$, 1 mM β-mercaptoethanol, 1 μM $^3$H-cAMP, 10 μM CI-930, PDE IV stock solution, and the desired concentration of test compound. CI-930 is included as an inhibitor of the cyclic GMP-sensitive, cyclic AMP-selective PDE (PDE III) that is also present in the PDE IV stock solution when prepared as described above. The ability of a test compound to inhibit PDE IV is determined by measuring the reduction in cAMP metabolism produced by the test compound and expressing it as a percentage of the reduction induced by 10 μM rolipram, a potent inhibitor of PDE IV [see Beavo, *Advances in Second Messenger and Phosphoprotein Research*, 22, 1 (1988)]. IC$_{50}$s are calculated for each test compound as the concentration of test compound that inhibits PDE IV by 50%.

Test Procedure No. 2

The following standard test is also employed to assess the abilities of compounds to inhibit PDE IV functionally.

Male Hartley guinea pigs (500–550 g, Charles River) were euthanized by a blow to the head, and the tracheas were removed and placed in aerated physiological salt solution (PSS) containing NaCl (118 mM), $KH_2PO_4$ (1.18 mM), KCl (4.74 mM), $CaCl_2$ (2.5 mM), $MgSO_4 \cdot 7H_2O$ (1.19 mM), $NaHCO_3$ (25 mM), dextrose (11.1 mM), cocaine and hydrocortisone (3 μM and 10 μM, respectively, to block intraneural and extraneural uptake mechanisms), propranolol and phentolamine (1 μM and 10 μM, respectively, to block adrenoceptors), indomethacin (2.8 μM; to block spontaneous tension generation), and calcium disodium EDTA (26 μM, as an antioxidant). Tracheal rings were prepared and mounted in 10 ml organ baths for the measurement of isometric tension generation as previously described (Heaslip et al., 1986).

Tracheal relaxation resulting from the inhibition of PDE-IV or PDE-III was assessed by a method similar to that employed by Harris et al. (1989). Tracheal rings were precontracted with 1 gM carbachol until a stable level of tension was obtained (30 min). To explore the inhibition of PDE-IV, tracheal rings were then incubated (45 min) with CI-930 (10 μM), thus inhibiting PDE-III and sensitizing the ring to the relaxant effects of PDE-IV inhibitors. Conversely, the inhibition of tracheal PDE-III was explored using rings pretreated with rolipram (10 μM), and thereby sensitized to PDE-III inhibitors (Harris et al., 1989). The functional inhibition of PDE-IV or PDE-III was determined by adding a test compound to the tissue bath in cumulatively increasing concentrations and monitoring the degree of relaxation induced in the continued presence of CI-930 or rolipram (respectively). After adding the final concentration of test compound to the organ bath, tracheal rings were washed repeatedly with PSS, and allowed to relax to resting tension. Percent relaxations produced by each concentration of test compound were calculated as a percentage relaxation of tension maintained in the presence of the preincubating PDE inhibitor, relative to the final resting tension determined at the end of each experiment.

The two abovementioned PDE IV inhibition tests were used to determine the PDE IV inhibitory abilities of some of the compounds of the present invention. The table below indicates the compounds tested and the results thereof. For each of Tests 1 and 2, the results are given as $IC_{50}$s for the compound tested in M concentrations.

TABLE

| Compound of Example # | Test No. 1 | Test No. 2 |
|---|---|---|
| 1 | $24.5 \times 10^{-8}$ | nt |
| 2 | $6.0 \times 10^{-8}$ | $16 \times 10^{-8}$ |
| 3 | $5.8 \times 10^{-8}$ | $6.6 \times 10^{-8}$ |
| 4 | $10 \times 10^{-8}$ | nt |
| 5 | $2.3 \times 10^{-8}$ | $6.1 \times 10^{-8}$ |
| 6 | $10 \times 10^{-8}$ | $1200 \times 10^{-8}$ |
| 7 | nt | nt |
| 8 | $3.4 \times 10^{-8}$ | $33 \times 10^{-8}$ |
| 9 | $2.0 \times 10^{-8}$ | $2.3 \times 10^{-8}$ |
| 10 | $10 \times 10^{-8}$ | nt |
| 11 | $0.43 \times 10^{-8}$ | nt |
| 12 | $8.6 \times 10^{-8}$ | nt |
| 13 | $61 \times 10^{-8}$ | nt |
| 14 | $8.4 \times 10^{-8}$ | nt |
| 15 | nt | nt |
| 16 | $33 \times 10^{-8}$ | nt |
| 17 | $11 \times 10^{-8}$ | nt |
| 18 | $3.1 \times 10^{-8}$ | $12 \times 10^{-8}$ |
| 19 | $58 \times 10^{-8}$ | nt |
| 20 | $5.9 \times 10^{-8}$ | nt |
| 21 | $29 \times 10^{-8}$ | nt |
| 22 | $3.6 \times 10^{-8}$ | $14 \times 10^{-8}$ |
| 23 | $3.9 \times 10^{-8}$ | $190 \times 10^{-8}$ |
| 24 | nt | nt |
| 25 | $73 \times 10^{-8}$ | nt |
| 26 | $27 \times 10^{-8}$ | nt |
| 27 | $55 \times 10^{-8}$ | nt |
| 28 | $100 \times 10^{-8}$ | nt |
| 29 | $47 \times 10^{-8}$ | nt |
| 30 | $1.6 \times 10^{-8}$ | nt |
| 31 | $10 \times 10^{-8}$ | nt |
| 32 | $1,000 \times 10^{-8}$ | nt |
| 33 | $110 \times 10^{-8}$ | nt |
| 34 | $4.9 \times 10^{-8}$ | nt |

(nt = not tested)

What is claimed:

1. A compound of the following structure:

wherein:

$R_1$ is $C_1$–$C_6$ alkyl, $C_3$–$C_6$ cycloalkyl, phenyl, or $C_1$–$C_4$ substituted phenyl;

$R_2$ is $C_3$–$C_6$ cycloalkyl, phenyl, or $C_3$–$C_{10}$ alkyl;

X,Y is O or S; and

W is selected from =O, =NOH, =NNH$_2$, =NOC(O)CH$_3$, or =NNHC(O)CH$_3$;

or a pharmaceutically acceptable salt thereof.

2. The compound of claim 1 wherein:

$R_1$=CH$_3$;

$R_2$=$C_4$ alkyl or $C_5$ cycloalkyl;

X,Y=O or S; and

W is selected from =O, =NOH, =NNH$_2$, =NOC(O)CH$_3$, or =NNHC(O)CH$_3$;

or a pharmaceutically acceptable salt thereof.

3. A compound of claim 1 wherein ring B is attached to ring A at the 5, 6, or 7 position of ring B, or a pharmaceutically acceptable salt thereof.

4. A compound of claim 1 which is 6-(3-Cyclopentyloxy-4-methoxy-phenyl)-3,4-dihydro-2H-napthalen-1-one.

5. A compound of claim 1 which is (E)-6-(3-Cyclopentyloxy-4-methoxy-phenyl)-3,4-dihydro-2H-naphthalen-1-one oxime.

6. A compound of claim 1 which is E-6-(3-Cyclopentyloxy-4-methoxy-phenyl)-3,4-dihydro-2H-naphthalen-1-one oxime acetate.

7. A method of treating asthma and allergic and inflammatory diseases in a mammal in need thereof, the method comprising administering to said mammal an effective amount of a compound having the formula:

wherein:

$R_1$ is $C_1$–$C_6$ alkyl, $C_3$–$C_6$ cycloalkyl, phenyl, or $C_1$–$C_4$ substituted phenyl;

$R_2$ is $C_3$–$C_6$ cycloalkyl, phenyl, or $C_3$–$C_{10}$ alkyl;

X,Y is O or S; and

W is selected from =O, =NOH, =NNH$_2$, =NOC(O)CH$_3$, or =NNHC(O)CH$_3$;

or a pharmaceutically acceptable salt thereof.

8. The method of claim 7 in which the compound is 6-(3-Cyclopentyloxy-4-methoxy-phenyl)-3,4-dihydro-2H-napthalen-1-one.

9. The method of claim 7 in which the compound is (E)-6-(3-Cyclopentyloxy-4-methoxy-phenyl)-3,4-dihydro-2H-naphthalen-1-one oxime.

10. The method of claim 7 in which the compound is E-6-(3-Cyclopentyloxy-4-methoxy-phenyl)-3,4-dihydro-2H-naphthalen-1-one oxime acetate.

11. A pharmaceutical composition for use in treating asthma and allergic and inflammatory diseases in a mammal in need thereof, the composition comprising an effective amount of a compound of the formula:

wherein:

$R_1$ is $C_1$–$C_6$ alkyl, $C_3$–$C_6$ cycloalkyl, phenyl, or $C_1$–$C_4$ substituted phenyl;

$R_2$ is $C_3$–$C_6$ cycloalkyl, phenyl, or $C_3$–$C_{10}$ alkyl;

X,Y is O or S; and

W is selected from =O, =NOH, =NNH$_2$, =NOC(O)CH$_3$, or =NNHC(O)CH$_3$;

or a pharmaceutically acceptable salt thereof, and a pharmaceutically acceptable carrier.

12. The pharmaceutical composition of claim 11 in which the compound is 6-(3-Cyclopentyloxy-4-methoxy-phenyl)-3,4-dihydro-2H-napthalen-1-one.

13. The pharmaceutical composition of claim 11 in which the compound is (E)-6-(3-Cyclopentyloxy-4-methoxy-phenyl)-3,4-dihydro-2H-naphthalen-1-one oxime.

14. The pharmaceutical composition of claim 11 in which the compound is E-6-(3-Cyclopentyloxy-4-methoxy-phenyl)-3,4-dihydro-2H-naphthalen-1-one oxime acetate.

15. A compound of the following structure:

wherein:

$R_1$ is $C_1$–$C_6$ alkyl, $C_3$–$C_6$ cycloalkyl, phenyl, or $C_1$–$C_4$ substituted phenyl;

$R_2$ is $C_3$–$C_6$ cycloalkyl, phenyl, or $C_3$–$C_{10}$ alkyl;

X and Y are O; and

W is O;

or a pharmaceutically acceptable salt thereof.

16. The compound of claim 15 wherein:

$R_1$=CH$_3$;

$R_2$=C$_4$ alkyl or C$_5$ cycloalkyl;

X,Y=O; and

W=O;

or a pharmaceutically acceptable salt thereof.

17. A method of treating asthma and allergic and inflammatory diseases in a mammal in need thereof, the method comprising administering to said mammal an effective amount of a compound having the formula:

wherein:

$R_1$=$C_1$–$C_6$ alkyl, $C_3$–$C_6$ cycloalkyl, phenyl, or $C_1$–$C_4$ substituted phenyl;

$R_2$=$C_3$–$C_6$ cycloalkyl, phenyl, or $C_3$–$C_{10}$ alkyl;

X and Y are O; and

W=O;

or a pharmaceutically acceptable salt thereof.

18. A pharmaceutical composition for use in treating asthma and allergic and inflammatory diseases in a mammal in need thereof, the composition comprising an effective amount of a compound of the formula:

wherein:

$R_1$=$C_1$–$C_6$ alkyl, $C_3$–$C_6$ cycloalkyl, phenyl, or $C_1$–$C_4$ substituted phenyl;

$R_2$=$C_3$–$C_6$ cycloalkyl, phenyl, or $C_3$–$C_{10}$ alkyl;

X and Y are O; and

W=O;

or a pharmaceutically acceptable salt thereof, and a pharmaceutically acceptable carrier.

* * * * *